US00PP16380P2

(12) United States Plant Patent
Hooijman

(10) Patent No.: US PP16,380 P2
(45) Date of Patent: Mar. 28, 2006

(54) ***ASTER* PLANT NAMED 'ESMNICARAGUA'**

(50) Latin Name: *Aster hybrida*
Varietal Denomination: Esmnicaragua

(75) Inventor: Aloysius A. J. Hooijman, Aalsmeer (NL)

(73) Assignee: Esmeralda Breeding B.V., Aalsmeer (NL)

( * ) Notice: Subject to any disclaimer, the term of this patent is extended or adjusted under 35 U.S.C. 154(b) by 157 days.

(21) Appl. No.: 10/919,001

(22) Filed: Aug. 16, 2004

(51) Int. Cl.
*A01H 5/00* (2006.01)

(52) U.S. Cl. ..... Plt./355
(58) Field of Classification Search ..... Plt./355
See application file for complete search history.

*Primary Examiner*—Kent Bell
(74) *Attorney, Agent, or Firm*—C. A. Whealy

(57) ABSTRACT

A new and distinct cultivar of cut flower *Aster* plant named 'Esmnicaragua', characterized by its strong and erect flowering stems; symmetrical branching habit with long lateral branches; dark green-colored foliage; uniform and freely flowering habit; daisy-type inflorescences with light purple-colored ray florets; and good postproduction longevity.

2 Drawing Sheets

Botanical classification/cultivar designation: *Aster hybrida* cultivar Esmnicaragua.

BACKGROUND OF THE INVENTION

The present Invention relates to a new and distinct cultivar of cut flower *Aster* plant, botanically known as *Aster hybrida* and hereinafter referred to by the name 'Esmnicaragua'.

The new *Aster* is a product of a planned breeding program conducted by the Inventor in El Quinche, Pichincha, Ecuador. The objective of the breeding program is to create new cut flower *Aster* cultivars with durable leaves, strong stems, desirable floret colors and good postproduction longevity.

The new *Aster* originated from a cross-pollination made by the Inventor in El Quinche, Pichincha, Ecuador in February, 2000, of a proprietary *Aster* selection identified as Line 04, not patented, as the female, or seed, parent with an unknown *Aster* selection, not patented, as the male or pollen, parent. The new *Aster* was discovered and selected by the Inventor as a single flowering plant within the progeny of the stated cross-pollination grown in a controlled environment in El Quinche, Pichincha, Ecuador. The selection of this plant was based on its durable foliage, strong stems and desirable inflorescence form and attractive ray floret color.

Asexual reproduction of the new *Aster* by vegetative tip cuttings was first conducted in El Quinche, Pichincha, Ecuador in January, 2001. Asexual reproduction by cuttings has shown that the unique features of this new *Aster* are stable and reproduced true to type in successive generations.

SUMMARY OF THE INVENTION

The cultivar Esmnicaragua has not been observed under all possible environmental conditions. The phenotype may vary somewhat with variations in environment such as temperature, daylength, and/or light level, without, however, any variance in genotype.

The following traits have been repeatedly observed and are determined to be the unique characteristics of 'Esmnicaragua'. These characteristics in combination distinguish 'Esmnicaragua' as a new and distinct cut flower *Aster:*

1. Strong and erect flowering stems.
2. Symmetrical branching habit with long lateral branches.
3. Dark green-colored foliage.
4. Uniform and freely flowering habit.
5. Daisy-type inflorescences with light purple-colored ray florets.
6. Good postproduction longevity.

Plants of the new *Aster* can be compared to plants of the female parent selection. Plants of the new *Aster* differ from plants of the female parent selection primarily in plant height as plants of the new *Aster* are shorter than plants of the female parent selection.

Plants of the new *Aster* can be compared to plants of the cultivar Claudia, not patented. In side-by-side comparisons conducted in El Quinche, Pichincha, Ecuador plants of the new *Aster* differed from plants of the cultivar Claudia in the following characteristics:

1. Plants of the new *Aster* were shorter than plants of the cultivar Claudia.
2. Plants of the new *Aster* had larger leaves than plants of the cultivar Claudia.
3. Plants of the new *Aster* were more freely flowering than plants of the cultivar Claudia.
4. Plants of the new *Aster* and the cultivar Claudia differed in ray floret coloration as plants of the cultivar Claudia had lighter purple-colored ray florets.

BRIEF DESCRIPTION OF THE PHOTOGRAPHS

The accompanying colored photographs illustrate the overall appearance of the new *Aster* showing the colors as true as it is reasonably possible to obtain in colored reproductions of this type. Colors in the photographs may differ from the color values cited in the detailed botanical description which accurately describe the colors of the new *Aster.*

The photograph on the first sheet comprises a side perspective view of a typical flowering plant of 'Esmnicaragua'.

The photograph on the second sheet are close-up views of a typical inflorescence of 'Esmnicaragua' (left) and a typical inflorescence of 'Claudia' (left).

DETAILED BOTANICAL DESCRIPTION

In the following description, color references are made to The Royal Horticultural Society Colour Chart, 2001 Edition, except where general terms of ordinary dictionary significance are used. The aforementioned photographs, folowing observations and measurements describe plants grown and flowered during the fall and winter in El Quinche, Pichincha, Ecuador, in an outdoor nursery and under conditions which approximate those generally used in commercial cut flower *Aster* production. During the production of these plants, day temperatures ranged from 12 to 30° C. and night temperatures ranged from 5 to 12° C. Plants were about four to six months from planting rooted young plants when the photographs and the botanical description were taken.

Botanical classification: *Aster hybrida* cultivar Esmnicaragua.

Parentage:

*Female, or seed, parent.*—Proprietary *Aster hybrida* selection identified as Line 04, not patented.

*Male, or pollen, parent.*—Unknown *Aster hybrida* selection, not patented.

Propagation:

*Type.*—Terminal vegetative cuttings.

*Time to initiate roots.*—About 12 to 16 days at 17 to 25° C.

*Time to produce a rooted young plant.*—About 21 to 25 days at 17 to 25° C.

*Root description.*—Fine, fibrous; 162D to 161D in color.

*Rooting habit.*—Freely branching.

Plant description:

*Appearance.*—Herbaceous daisy-type cut flower *Aster*. Flowering stems upright and strong. Vigorous. Symmetrical branching habit with long lateral branches.

*Plant height.*—About 77 cm.

*Plant width.*—About 23 cm.

*Lateral branches.*—Quantity per plant: About 18. Length: About 42 cm. Diameter: About 2.7 mm. Internode length: About 2.2 cm. Strength: Moderately strong. Texture: Smooth, initially pubescent, becoming glabrous with development; waxy. Color: 144C overlain with 183C.

*Foliage description.*—Arrangement: Alternate, simple; sessile. Length: About 12.4 cm. Width: About 1.8 cm. Shape: Lanceolate. Apex: Acute. Base: Cordate. Margin: Finely serrate. Texture, upper and lower surfaces: Glabrous, smooth; waxy. Color: Developing foliage, upper surface: 147A to 139A. Developing foliage, lower surface: 137A to 147A. Fully expanded foliage, upper surface: 137A to 147A; venation, 146B to 147B. Fully expanded foliage, lower surface: 137B to 146A; venation, 146C to 147B.

Inflorescence description:

*Appearance.*—Daisy-type inflorescence form with narrowly elliptic-shaped ray florets. Inflorescences terminal or axillary. Disc and ray florets develop acropetally on a capitulum. Inflorescences not fragrant. Inflorescences persistent. Inflorescences face mostly upright. Uniform and freely flowering habit.

*Flowering response.*—Plants flower year-round in Ecuador. Plants begin flowering about 14 to 15 weeks after planting.

*Postproduction longevity.*—Inflorescences maintain good color and substance for about 10 to 12 days as a cut flower and about 25 days on the plant.

*Quantity of inflorescences.*—About 15 inflorescences develop per lateral branch.

*Inflorescence bud.*—Height: About 6 mm. Diameter: About 5 mm. Shape: Nearly globose. Color: 137A to 145B.

*Inflorescence size.*—Diameter: About 3.2 cm. Depth (height): About 1.2 cm. Diameter of disc: About 1.1 cm. Receptacle height: About 7 mm. Receptacle diameter: About 9 mm.

*Ray florets.*—Number of ray florets per inflorescence/arrangement: About 96 in arranged in two or three whorls. Length: About 1.5 cm. Width: About 3 mm. Shape: Narrowly elliptic. Apex: Obtuse with emarginations. Base: Attenuate. Margin: Entire. Texture, upper and lower surfaces: Smooth, glabrous; papery. Orientation: Initially upright, then mostly horizontal. Aspect: Mostly straight. Color: When opening, upper surface: 72C to 70B. When opening, lower surface: N78D to N74C. Fully opened, upper surface: N74C to N78C; color becoming closer to 76A with development. Fully opened, lower surface: 75A to 77C.

*Disc florets.*—Arrangement: Massed at center of receptacle. Number of disc florets per inflorescence: About 47. Length: About 1 cm. Diameter, apex: About 1.7 mm. Diameter, base: About 0.6 mm. Shape: Tubular, salverform, elongated. Apex: Five lobes; lobes acute. Color, immature: 154B. Color, mature: Apex: 1A to 1B. Mid-section and base: 145C to 149D.

*Phyllaries.*—Quantity per inflorescence: About 59. Length: About 4 mm. Width: About 1.1 mm. Shape: Narrowly deltoid. Apex: Acute. Base: Truncate. Texture, upper and lower surfaces: Smooth, glabrous. Color, upper surface: 137B to 145B. Color, lower surface: 137A to 145B.

*Peduncles.*—Length, terminal peduncle: About 4 mm. Length, fourth peduncle: About 1.8 cm. Length, seventh peduncle: About 2.9 cm. Diameter: About 1 mm. Aspect: Erect to about 30° from vertical. Strength: Strong. Texture: Pubescent. Color: 137B to 146A.

*Reproductive organs.*—Androecium: Present on disc florets only. Quantity per disc floret: One. Anther shape: Linear. Anter length: About 1.5 mm. Anther color: Towards the apex, 174A; towards the base, 2B. Pollen amount: Scarce. Pollen color: 2B. Gynoecium: Present on both ray and disc florets. Quantity per floret: One. Pistil length: About 9 mm. Stigma shape: Bilobed; lobes linear. Stigma color: 145C to 151D. Style length: About 7.4 mm. Style color: 145D to 149D. Ovary color: 157D.

*Seed.*—Length: With pappus, about 5 mm; without pappus, about 3 mm. Diameter: About 1 mm. Color: 145D; dried, 199A.

Disease/pest resistance: Resistance to pathogens and pests common to *Asters* has not been observed on plants grown under commercial greenhouse conditions.

Temperature tolerance: Plants of the new *Aster* have been observed to tolerate temperatures from about 7 to about 30° C.

It is claimed:

1. A new and distinct cultivar of cut flower *Aster* plant named 'Esmnicaragua', as illustrated and described.

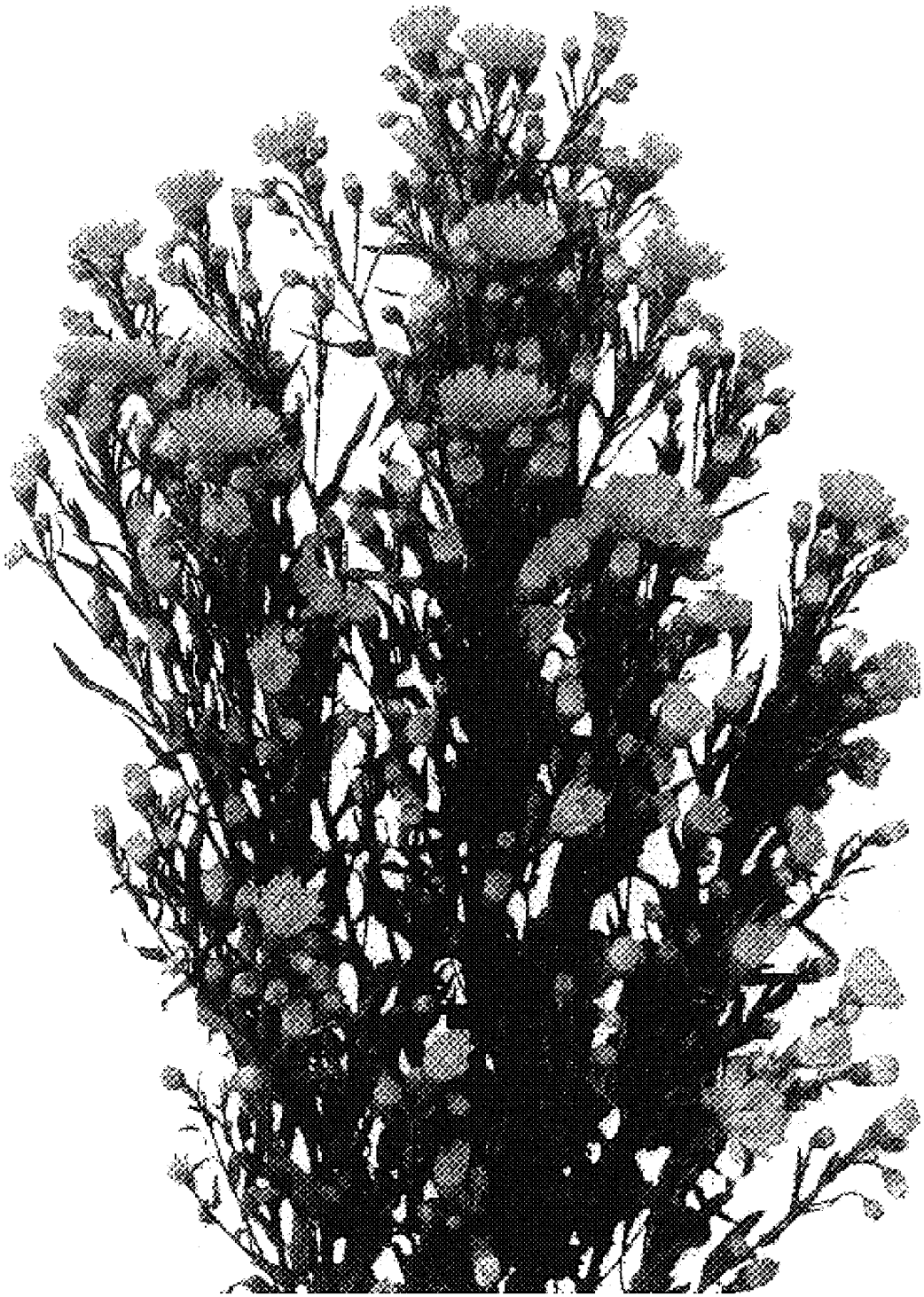

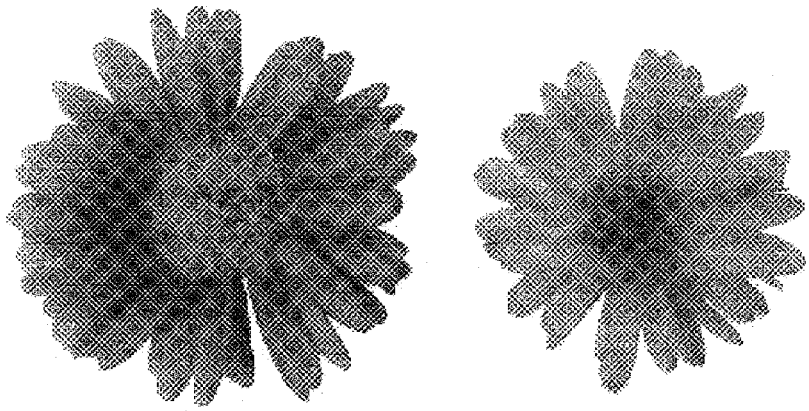

* * * * *